US012650414B2

(12) United States Patent
Huang

(10) Patent No.: US 12,650,414 B2
(45) Date of Patent: Jun. 9, 2026

(54) PHOTOIONIZATION DETECTOR SENSOR UTILIZING TIME DIVISION MODES TO PERFORM SEPARATION AND DETECTION IN THE SAME PHYSICAL REGION

(71) Applicant: HONEYWELL INTERNATIONAL INC., Charlotte, NC (US)

(72) Inventor: Chuang Huang, Charlotte, NC (US)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 423 days.

(21) Appl. No.: 18/450,820

(22) Filed: Aug. 16, 2023

(65) Prior Publication Data

US 2024/0068999 A1     Feb. 29, 2024

(30) Foreign Application Priority Data

Aug. 30, 2022     (CN) .......................... 202211046212.4

(51) Int. Cl.
G01N 33/00          (2006.01)

(52) U.S. Cl.
CPC ..... G01N 33/0047 (2013.01); G01N 33/0062 (2013.01)

(58) Field of Classification Search
CPC ....................... G01N 33/0047; G01N 33/0062
See application file for complete search history.

(56) References Cited

U.S. PATENT DOCUMENTS

| | | | |
|---|---|---|---|
| 6,509,562 B1 | 1/2003 | Wenjun et al. | |
| 7,148,477 B2 | 12/2006 | Miller et al. | |
| 8,440,968 B2 | 5/2013 | Giles | |
| 9,564,290 B2 | 2/2017 | Burchfield | |
| 9,683,963 B2 | 6/2017 | Verenchikov | |

(Continued)

FOREIGN PATENT DOCUMENTS

| | | |
|---|---|---|
| CN | 112509908 A | 3/2021 |
| DE | 102020132851 B3 | 12/2021 |
| WO | 2013/173320 A1 | 11/2023 |

OTHER PUBLICATIONS

Decision to grant a European patent Mailed on Mar. 20, 2025 for EP Application No. 23188904, 2 page(s).

(Continued)

*Primary Examiner* — Sean M Luck
(74) *Attorney, Agent, or Firm* — Alston & Bird LLP

(57)          ABSTRACT

A method, apparatus, and computer program product for detecting volatile organic compounds (VOCs) in a gas is provided. An example VOC detector may include a processing device and a detecting region. The detecting region may further include a first interdigital pole electrically connected to a separation voltage source, a second interdigital pole electrically connected to a switch, and an ionization device configured to interact with the gas within the detecting region to create a plurality of ionized gas molecules. To facilitate detection of VOCs, the switch may alternate the connection of the second interdigital pole between a compensation voltage source and the processing device. The processing device may determine a number of volatile organic compounds in the gas based at least in part on a number of ionized gas molecules that contact the second interdigital pole while the second interdigital pole is electrically connected to the processing device.

20 Claims, 8 Drawing Sheets

(56)          References Cited

U.S. PATENT DOCUMENTS

| | | | |
|---|---|---|---|
| 9,772,307 B2 * | 9/2017 | Mitko | G01N 27/622 |
| 2008/0191132 A1 | 8/2008 | Boyle et al. | |
| 2015/0108345 A1 * | 4/2015 | Fujita | H01J 49/062 |
| | | | 250/286 |
| 2022/0178875 A1 | 6/2022 | Beyer et al. | |

OTHER PUBLICATIONS

Communication about intention to grant a European patent Mailed on Nov. 19, 2024 for EP Application No. 23188904, 6 page(s).
Extended European Search Report Mailed on Jan. 29, 2024 for EP Application No. 23188904, 7 page(s).

* cited by examiner

412

700

708

710

716

706

712

714

704

702

ON

OFF

TO V2
TO SIGNAL PROCESSING CIRCUIT

TIME(ms)

PHOTOIONIZATION DETECTOR SENSOR UTILIZING TIME DIVISION MODES TO PERFORM SEPARATION AND DETECTION IN THE SAME PHYSICAL REGION

CROSS-REFERENCE TO RELATED APPLICATIONS

This application claims priority pursuant to 35 U.S.C. 119(a) to Chinese Application No. 202211046212.4, filed Aug. 30, 2022, which application is incorporated herein by reference in its entirety.

TECHNOLOGICAL FIELD

Embodiments of the present disclosure relate generally to photoionization detector sensors (PID sensors), more specifically, to photoionization detector sensors utilizing field asymmetric ion mobility spectrometry (FAIMS) techniques to measure the presence of volatile organic compounds (VOCs) in a gas.

BACKGROUND

Applicant has identified many technical challenges and difficulties associated with the operation of PID sensors utilizing FAIMS techniques. Through applied effort, ingenuity, and innovation, Applicant has solved problems related to the structure and operation of PID sensors by developing solutions embodied in the present disclosure, which are described in detail below.

BRIEF SUMMARY

Various embodiments are directed to an example method, apparatus, and computer program product for utilizing a PID sensor, leveraging differences in high-field and low-field ion mobility of target VOCs, to detect VOCs in a gas.

In accordance with some embodiments of the present disclosure, an example PID sensor for detecting VOCs in a gas is provided. In some embodiments, the PID VOC sensor may comprise a processing device and a detecting region. The detecting region may further comprise a first interdigital pole disposed within the detecting region and electrically connected to a separation voltage source, a second interdigital pole disposed within the detecting region and electrically connected to a switch, and an ionization device configured to interact with the gas within the detecting region creating a plurality of ionized gas molecules, wherein the switch alternates the connection of the second interdigital pole between a compensation voltage source and the processing device. Further, the processing device may determine a VOC value representative of a number of volatile organic compounds in the gas based at least in part on a number of ionized gas molecules that contact the second interdigital pole while the second interdigital pole is electrically connected to the processing device.

In some embodiments, the PID VOC sensor may further comprise a housing comprising a base, wherein the processing device is attached to the housing at or near the base, and a housing wall protruding from the base forming an enclosed perimeter around an interior cavity and defining an opening opposite the base. In some embodiments, the switch may be positioned in the interior cavity and attached to the housing, and the ionization device may be disposed proximate the base and directed toward the opening. The PID VOC sensor may further comprise a cap detachably connected to the housing wall, substantially covering the opening and further comprising a vent, wherein the gas enters the housing through the vent, wherein the detecting region may be positioned inside the interior cavity of the housing between the vent in the cap of the housing and the ionization device. The PID VOC sensor may further comprise a first electrical connector disposed on the exterior of the housing and providing electrical connectivity from the separation voltage source to the interior cavity of the housing and a second electrical connector disposed on the exterior of the housing and providing electrical connectivity from the compensation voltage source to the interior cavity of the housing. In some embodiments, the first interdigital pole of the detecting region may be electrically connected to the first electrical connector, and the switch may be positioned inside the interior cavity of the housing and alternate an electrical connection from the second electrical connector and the processing device to the second interdigital pole of the detecting region.

In some embodiments, the first and second interdigital poles each comprise a plurality of comb-like conducting prongs, wherein the prongs of the first interdigital pole may be directed toward the prongs of the second interdigital pole, and wherein the second interdigital pole may offset from the first interdigital pole such that the prongs of the first interdigital pole occupy a space between the prongs of the second interdigital pole.

In some embodiments, the PID VOC sensor may operate in at least three time phases, an ionization phase wherein gas molecules of the gas are exposed to the ionization device, a separation phase wherein a separation voltage is applied to the first interdigital pole, and a detection phase wherein the switch is positioned to electrically connect the second interdigital pole to the processing device.

In some embodiments, the ionization phase and the separation phase may substantially overlap.

In some embodiments, the ionization device may be an ultraviolet lamp projecting into the detecting region, and gas molecules with an ionization potential lower than ionization energy of the UV light may be ionized.

In some embodiments, the ultraviolet lamp may be substantially on during the ionization phase and substantially off during the detection phase.

In some embodiments, the switch may be a single pole double throw switch having an input side with a single input connector and an output side having a first output connector and a second output connector, wherein the single input connector is electrically connected to the second interdigital pole, the first output connector is electrically connected to the compensation voltage source, and the second output connector is electrically connected to the processing device.

In some embodiments, the detection phase may be defined by the switch providing an electrical connection between the second interdigital pole and the processing device, a first constant DC voltage supplied to the first interdigital pole and a second constant DC voltage is supplied to the second interdigital pole, and the ionization device being disabled.

In some embodiments, the separation voltage source may provide an alternating current to the first interdigital pole during the separation phase and otherwise supply a constant direct current voltage to the first interdigital pole.

In some embodiments, the compensation voltage source may be a direct current voltage.

An example method for detecting volatile organic compounds (VOCs) in a gas diffused into a detecting region of a VOC sensor is further provided. In some embodiments, the method may comprise executing an ionization phase comprising, exposing the gas to an ionization device creating a plurality of ionized gas molecules. The method may further comprise executing a separation phase comprising, supplying a separation voltage to a first interdigital pole disposed within the detecting region and electrically connected to a separation voltage source, and supplying a compensation voltage to a second interdigital pole disposed within the detecting region and electrically connected to a compensation voltage source through a switch. In some embodiments, the method may further comprise disabling the ionization device upon completion of the ionization phase. Further, in some embodiments, the method may further comprise executing a detection phase comprising, switching the switch to electrically connect the second interdigital pole to a processing device, supplying a first direct current voltage to the first interdigital pole and supplying a second direct current voltage to the second interdigital pole, and determining a VOC value representative of a number of volatile organic compounds in the gas based at least in part on a number of ionized gas molecules that contact the second interdigital pole while the second interdigital pole is electrically connected to the processing device.

In some embodiments, the first and second interdigital poles may each comprise a plurality of comb-like conducting prongs, wherein the prongs of the first interdigital pole are directed toward the prongs of the second interdigital pole, and wherein the second interdigital pole is offset from the first interdigital pole such that the prongs of the first interdigital pole occupy a space between the prongs of the second interdigital pole.

In some embodiments, the ionization phase and the separation phase may substantially overlap.

In some embodiments, the ionization device may be an ultraviolet (UV) lamp projecting into the detecting region, and gas molecules with an ionization potential lower than UV light may be ionized.

In some embodiments, the switch may be a single pole double throw switch having an input side with a single input connector and an output side having a first output connector and a second output connector, and the single input connector is electrically connected to the second interdigital pole, the first output connector is electrically connected to the compensation voltage source, and the second output connector is electrically connected to the processing device.

In some embodiments, the separation voltage source may provide an alternating current to the first interdigital pole during the separation phase and the separation voltage source may otherwise supply a constant direct current voltage to the first interdigital pole.

In some embodiments, the compensation voltage source may be a direct current voltage.

In some embodiments, the detection phase may further comprise altering the second direct current voltage that is supplied to the second interdigital pole.

An example computer program product for detecting volatile organic compounds (VOCs) in a gas diffused into a detecting region of a VOC sensor is also provided. In some embodiments, the computer program product may comprise at least one non-transitory computer-readable storage medium having computer-readable program code portions stored therein, the computer-readable program code portions comprising an executable portion configured to execute an ionization phase comprising enabling an ionization device and creating a plurality of ionized gas molecules. The executable portion may further be configured to execute a separation phase comprising causing a separation voltage to be supplied to a first interdigital pole disposed within the detecting region and electrically connected to a separation voltage source, and causing a compensation voltage to be supplied to a second interdigital pole disposed within the detecting region and electrically connected to a compensation voltage source through a switch. The executable portion may further be configured to disable the ionization device upon completion of the ionization phase. In addition, the executable portion may further be configured to execute a detection phase comprising toggling the switch to electrically connect the second interdigital pole to a processing device, and causing a first direct current voltage to be supplied to the first interdigital pole and cause a second direct current voltage to be supplied to the second interdigital pole. The executable portion may further be configured to determine a VOC value representative of a number of volatile organic compounds in the gas based at least in part on a number of ionized gas molecules that contact the second interdigital pole while the second interdigital pole is electrically connected to the processing device.

BRIEF DESCRIPTION OF THE DRAWINGS

Reference will now be made to the accompanying drawings. The components illustrated in the figures may or may not be present in certain embodiments described herein. Some embodiments may include fewer (or more) components than those shown in the figures in accordance with an example embodiment of the present disclosure.

DETAILED DESCRIPTION

Figure 1:
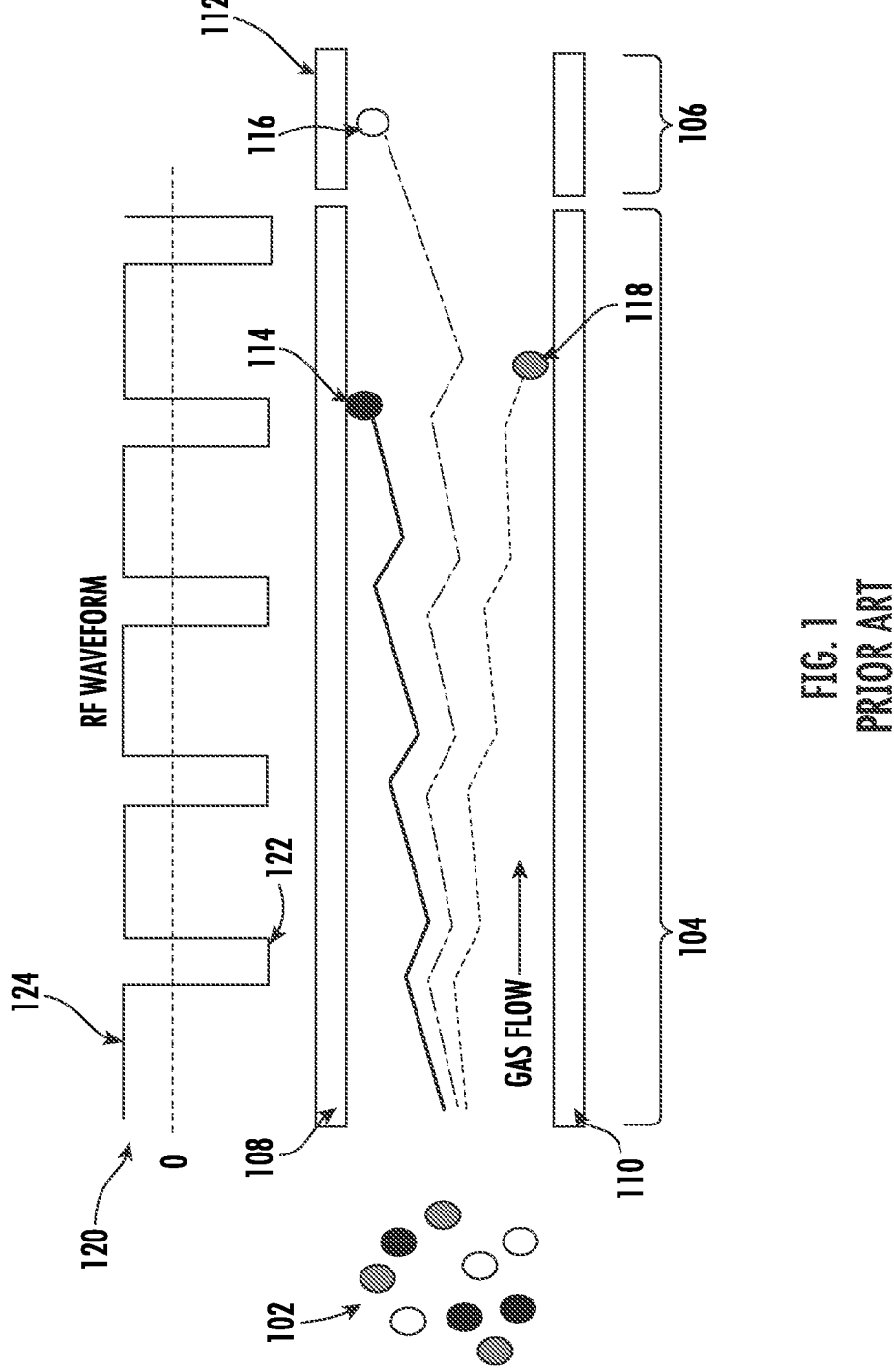
FIG. 1 illustrates a diagram of the ion detection process of an example prior art PID VOC sensor, in accordance with an example embodiment of the present disclosure.

Example embodiments will be described more fully hereinafter with reference to the accompanying drawings, in which some, but not all embodiments of the inventions of the disclosure are shown. Indeed, embodiments of the disclosure may be embodied in many different forms and should not be construed as limited to the embodiments set forth herein; rather, these embodiments are provided so that this disclosure will satisfy applicable legal requirements Like numbers refer to like elements throughout.

Various example embodiments address technical problems associated with detecting volatile organic compounds (VOCs) in a gas. As understood by those of skill in the field to which the present disclosure pertains, there are numerous example scenarios in which a user may need to a detect the presence and/or concentration of VOCs in a gas (e.g., air).

Volatile organic compounds are substances associated with a low boiling point at room temperature resulting in molecules that are susceptible to ready release into the surrounding air. VOCs released into the air can be dangerous to human health or to the environment. For example, substances such as solvents and paint thinners, as well as vapors associated with fuel and oil may release VOCs into the surrounding environment creating smog and generating ozone. VOCs inhaled by humans and animals can have adverse health effects such as causing irritation, allergies, damage to organs and the nervous system, and even cancer. In addition, a detectable amount of VOCs may be released from drugs, explosives, and chemical weapons, indicating the presence of these objects in a particular environment.

Photoionization detector (PID) sensors may detect the presence of VOCs through a technique known as ion mobility spectrometry (IMS). IMS exploits the differing mobility of ionized molecules in a gas, including VOCs, to separate a targeted VOC from other ionized and non-ionized molecules. Once separated, a device utilizing IMS techniques may measure the presence of ionized modules based on the voltage produced on an electrical conductor. High-field asymmetric-waveform ion-mobility spectrometry, or FAIMS, is another technique that takes advantage of the differing ion mobilities to separate ionized gas molecules. Specifically, FAIMS leverages the property present in many ionized molecules that the mobility of the ionized molecule is different in the presence of a high electric field versus a low electric field. PID detectors utilizing FAIMS techniques may pass the gas potentially containing VOCs through a varying electric field. Ionized molecules that are not targeted will drift toward one or the other of the electrodes where they will be neutralized upon contact. While targeted molecules will move through the separation region without impacting either electrode. Molecules that pass through the separation region without being neutralized will pass into the detecting region where the number of remaining molecules will be detected in the detecting region based on the electrical voltage produced by their presence. Detecting the presence of VOCs in gasses can be an important tool in identifying air-born molecules that are harmful to humans and/or the environment, or even indicate the presence of dangerous and/or illegal items.

However, many traditional VOC detectors can be too large or cumbersome for intended mobile uses. Many VOC detectors require a carrier gas to drive the potential VOC containing gas through a separating region. This type of setup generally requires a flow meter and pump which may add to the overall size and complexity of the device. In addition, VOC detectors utilizing FAIMS techniques require multiple sets of electrodes to separate the ionized molecules and separately detect the separated target molecules, further adding to the size and complexity of the device. Further, traditional VOC detectors must expose the gas to an ionization source in a separate region, resulting in loss of ions even before entering the separating region. Finally, VOC detectors generally require an ionization source which is constantly enabled, decreasing the project life of the device.

The various example embodiments described herein utilize various techniques to improve the detection of VOCs in a gas using FAIMS techniques. For example, in some embodiments, a PID VOC sensor in accordance with the present disclosure may utilize a single set of electrodes to perform separation and detection. In addition, ionization, separation, and detection may all occur in the same physical region. Confining these phases of VOC detection to the same region may be made possible, in some embodiments, by attaching at least one of the electrodes to a switch, which alternates power between a compensation voltage source and a processing device. This allows the electrode to fulfill the role of separating the ionized molecules according to mobility when connected to the compensation voltage source and detecting/counting the target molecules when switched to the processing device. By confining each of these steps to the same physical region, the overall architecture of the PID VOC sensor may be simplified and the overall size reduced. Further, ionizing the gas molecules in the same physical location as the separating and detecting region reduces the number of ions lost, improving the overall accuracy of the sensor.

In addition, in some embodiments disclosed herein, switching at least one electrode between a compensation voltage source and a processing device allows the PID VOC sensor described herein to switch on and off the ionization source. In embodiments wherein the ionization source is a UV lamp, or similar device, switching off the ionization source during the detection phase prolongs the life of the device.

As a result of the herein described example embodiments and in some examples, the effectiveness of a PID VOC sensor in detecting target VOC materials may be greatly improved. In addition, the size and overall complexity of the architecture may be reduced, facilitating use of the PID VOC sensor in diverse mobile and fixed embodiments.

FIG. 1 illustrates an example prior art process for VOC detection using a PID sensor utilizing FAIMS techniques. As shown in FIG. 1, the example prior art PID VOC sensor utilizes a process that includes a separation region 104 followed by a detection region 106. The separation region 104 includes two electrodes (e.g., first electrode 108 and second electrode 110), substantially parallel to each other and generating an electric field between them according to a waveform similar to separation radio frequency (RF) waveform 120. In addition, an ionization source 102 interacts with the gas molecules prior to entering the separation region 104, ionizing gas molecules with an ionization potential less than the energy emitted by the ionization source 102. After exposure to the ionization source 102, the ionized gas flows through the separation region 104, from the ionization source 102 toward the detection region 106, between the first electrode 108 and the second electrode 110. The detection region 106 includes a second set of one or more electrodes (e.g., detecting electrode 112) which determine the presence of ionized molecules (e.g., detected ion 116) based on the electric voltage generated by the presence of the ionized particles. Ionized particles (e.g., separated ion 114 and separated ion 118) which drift toward the electrodes in the separation region 104 and contact one of the electrodes (e.g., first electrode 108 and second electrode 110) are neutralized and not detected.

As shown in FIG. 1, the example prior art process for VOC detection using a PID sensor utilizing FAIMS techniques includes a separation region 104 physically distinct from the detection region 106. In order to separate target ions (e.g., detected ion 116) the ionized gas most flow through the separation region 104 at a regulated rate. This regulated flow of gas often requires additional equipment, such as a flow meter and/or pump. As such, gas particles are exposed to the ionization source 102 previous to entering the separation region 104. Exposure to the ionization source 102 previous to entering the separation region 104, and subsequent travel through the separation region 104 may result in ion loss due to diffusion, adversely affecting the detection of VOCs. In addition, physically separate separation regions 104 and detection regions 106 require an additional electrode, or electrodes. A first set of electrodes (e.g., first electrode 108 and second electrode 110), as shown in FIG. 1, are required to oscillate the electric field according to separation RF waveform 120 or a similar waveform, while a second set of electrodes (e.g., detecting electrode 112) are required to accurately determine the presence of VOCs due to the electric voltage generated by the presence of ionized molecules (e.g., detected ion 116).

Figure 2:
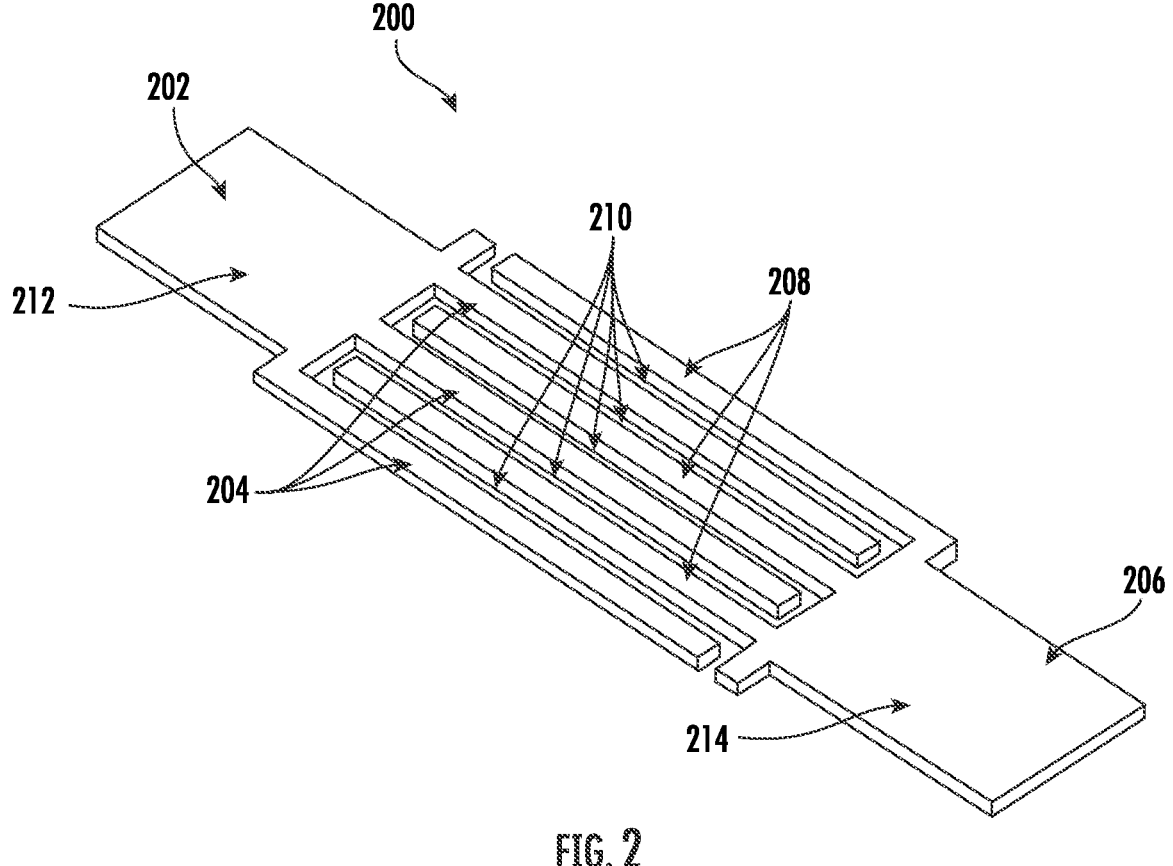
FIG. 2 illustrates an example interdigital pole conducting element of a PID VOC sensor, in accordance with an example embodiment of the present disclosure.

Referring now to FIG. 2, an example interdigital pole conducting component 200 is provided. The depicted example interdigital pole conducting component 200 of FIG. 2, shows a first interdigital pole 202 comprising a first conducting pad 212 and a first plurality of conducting prongs 204 projecting out from the first conducting pad 212 in parallel, comb-like prongs. Additionally, a second interdigital pole 206 is further provided comprising a second conducting pad 214 and a second plurality of conducting prongs 208 projecting out from the second conducting pad 214 also in parallel, comb-like prongs. The first interdigital pole 202 is positioned such that the first plurality of conducting prongs 204 are extending from the first conducting pad 212, towards the second interdigital pole 206 while the second plurality of conducting prongs 208 are extending from the second conducting pad 214 toward the first interdigital pole 202. The second interdigital pole 206 is positioned such that the second plurality of conducting prongs 208 are offset from the first plurality of conducting prongs 204 and substantially parallel to the first plurality of conducting prongs 204. Further, the first interdigital pole 202 and the second interdigital pole 206 are positioned such that the furthest extent of the first plurality of conducting prongs 208 extend past the furthest extent of the second plurality of conducting prongs 204, forming narrow gaps (e.g., electric field region 210) between the first set of conducting prongs 204 and the second set of conducting prongs 208. In operation, an electric charge may be applied to the first conducting pad 212 of the first interdigital pole 202 and the second conducting pad 214 of the second interdigital pole 206 generating an electric field in the plurality of electric field regions 210.

As depicted in FIG. 2, the example interdigital pole conducting component 200 includes a plurality of interdigital poles (e.g., first interdigital pole 202 and second interdigital pole 206). An interdigital pole may be any conducting or semi-conducting material, or a combination of conducting, semi-conducting, and insulating materials, such that when an electric charge is applied to a conducting pad (e.g., first conducting pad 212 and second conducting pad 214), the electric charge is transmitted on or along each of the plurality of conducting prongs (e.g., first plurality of conducting prongs 204 and second plurality of conducting prongs 208).

A PID sensor implementing FAIMS techniques separates ions based on the ion mobility in differing electric fields. An ions mobility (K) is the average velocity with which a given ion drifts when influenced by an electric field. Ions generated from different compounds may each have a different mobility when exposed to an electric field, meaning different ions will travel farther when exposed to the same electric field for the same amount of time. In addition, an ion may have a different mobility based on the intensity of an electric field (e.g., $K_h$ for a high electric field $E_h$, and $K_1$ for a low electric field $E_1$ such that $K_h \neq K_1$). For example, an ion may travel a farther distance when influenced by a high electric field then when influenced by a low electric field, even when the duration of exposure to each electric field (e.g., t h for the high electric field and $t_1$ for the low electric field) is adjusted such that the product of the magnitude of the electric field and the duration of that electric field are equal (e.g., $E_h t_h = E_1 t_1$).

Common FAIMS implementations will apply an asymmetric waveform (e.g., separation RF waveform 120), or separation voltage, to a first electrode, for example, first interdigital pole 202. A separation voltage, may be composed of a repeating pattern, including a high voltage component lasting for a short period of time and a lower voltage component of opposing polarity lasting for a longer period of time. Thus, when the separation voltage is applied to a first electrode, for example, first interdigital pole 202, VOCs will drift either toward or away from the interdigital pole based on the ratio of the mobility of the ion in the presence of a high electric field to the mobility of the ion in the presence of a low electric field ($K_h/K_1$). However, PID sensors utilizing FAIMS techniques may also apply a compensation voltage, or direct current (DC) voltage, to a second electrode, for example, interdigital pole 206. A compensation voltage is calculated to correct the drift of targeted ions. The compensation voltage allows the targeted ions to oscillate back and forth in the space between the two electrodes without contacting either one, while the non-targeted ions drift toward one or the other electrode. The compensation voltage may be updated or changed throughout the separation process, or in subsequent separation processes to target VOCs with different mobility properties.

Thus, by applying a separation voltage to the first interdigital pole 202 and a compensation voltage to the second interdigital pole 206, an oscillating electric field is generated in the electric field region 210. This oscillating electric field, in the space between the first interdigital pole 202 and the second interdigital pole 206, causes the targeted ions to remain in the space between the interdigital poles, while the non-targeted ions drift toward and contact one of the interdigital poles. By applying this technique, the targeted ions alone remain in the electric field region 210.

Figure 3:
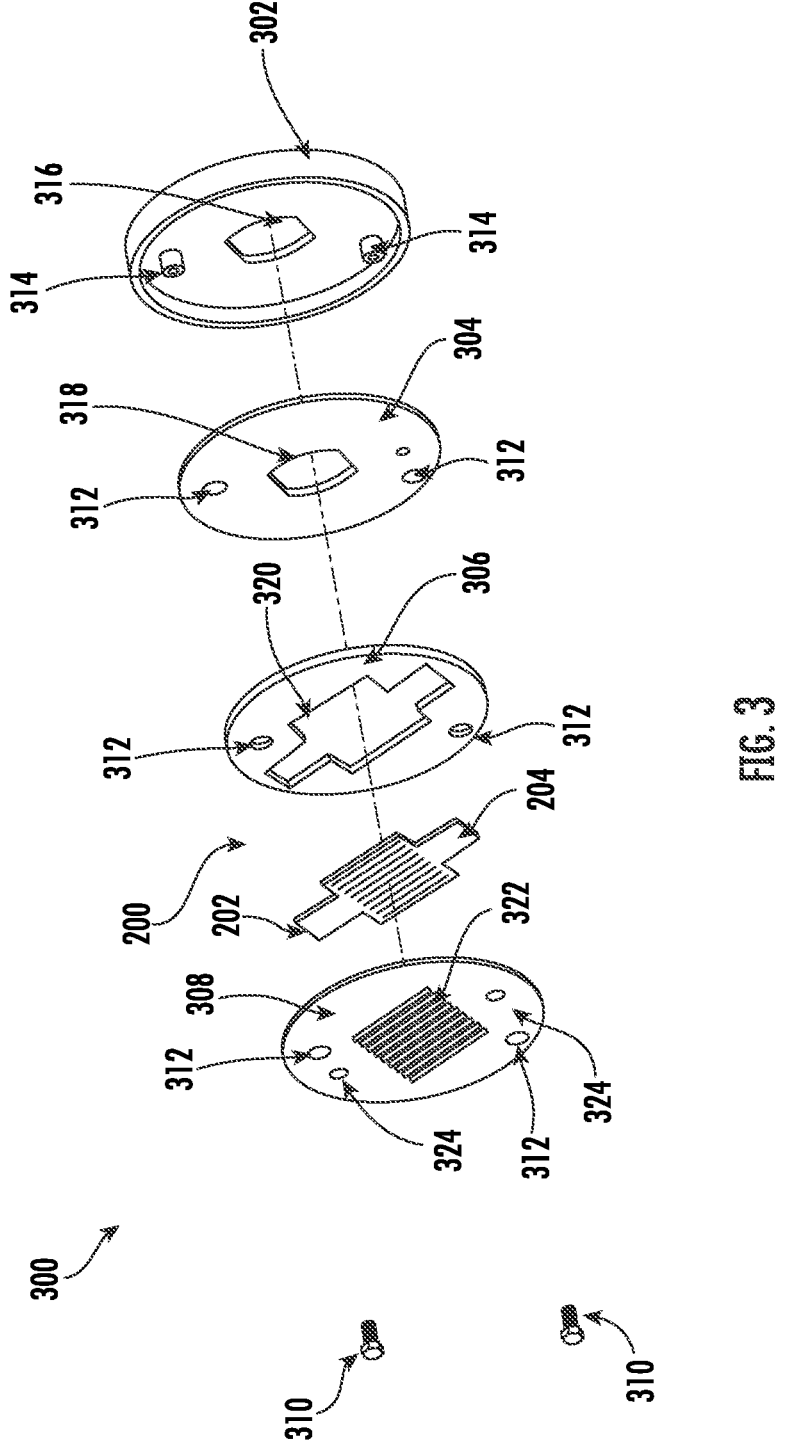
FIG. 3 illustrates an exploded view of an interdigital pole component of an example PID VOC sensor, in accordance with an example embodiment of the present disclosure.

Referring now to FIG. 3, an example interdigital pole component 300 is depicted. As depicted in FIG. 3, the example interdigital pole component 300 includes an interdigital pole conducting component 200.

The interdigital pole conducting component 200 is placed within an interdigital pole holder 306. The interdigital pole holder 306 includes an opening (e.g., interdigital poles cutout 320) substantially similar to the shape of the interdigital pole conducting component 200, receiving the interdigital pole conducting component 200 in a position which allows the interdigital poles to receive ion exposure from an ionization source 102 and receive the input gas from an exterior environment.

As further depicted in FIG. 3, the interdigital pole holder 306 and the interdigital pole conducting component 200 are disposed between the interdigital pole top cover 304 and the interdigital pole bottom cover 308 such that the interdigital pole conducting component 200 is forced into the interdigital poles cutout 320 in the interdigital pole holder 306. The interdigital pole top cover 304 further includes an opening (e.g., top cover opening 318) which allows gas to flow in and enter the electric field region 210 of the interdigital pole conducting component 200.

The interdigital pole bottom cover 308 further includes an interdigital poles exposure window 322, allowing an ion source such as a ultraviolet (UV) lamp to ionize the incoming gas. In addition, the interdigital pole bottom cover 308 includes electrical connecter openings 324. The electrical connector openings allow electrical conductors, such as pogo pins, to pass through the interdigital pole bottom cover 308 and contact each of the interdigital poles at first conducting pad 212 and second conducting pad 214.

Each of the interdigital pole bottom cover 308, interdigital pole holder 306, and interdigital pole top cover 304 further include screw holes 312 through which screws (e.g., screws 310) pass. In operation, the screws 310 align the openings in the surrounding covers with the interdigital pole conducting component 200. Further, the screws 310 compress the interdigital pole conducting component 200 between the interdigital pole bottom cover 308 and interdigital pole top cover 304 holding the interdigital pole conducting component 200 in the interdigital poles cutout 320.

As further depicted in FIG. 3, the example interdigital pole component 300 includes an interdigital pole housing 302 comprising an interdigital pole housing opening 316. The interdigital pole housing 302 further includes screw receivers 314 allowing the screws 310 to attach to the interdigital pole housing 302. Once attached, the screws 310 work to fasten the interdigital pole bottom cover 308, the interdigital pole holder 306 with the interdigital pole conducting component 200 disposed therein, and the interdigital pole top cover 304 against the interdigital pole housing 302 and within the cavity created by the interdigital pole housing 302. The interdigital pole housing opening 316 allows gas to disperse into the interdigital pole component 300 and into the electric field region 210 of the interdigital pole conducting component 200.

Figure 4A:
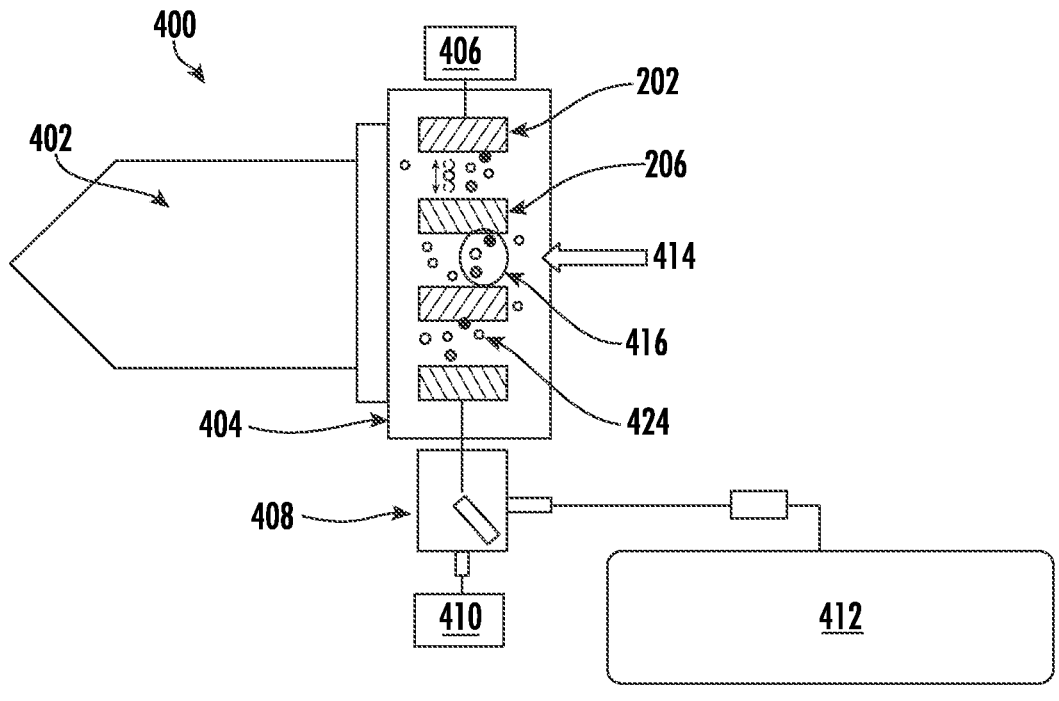
FIG. 4A illustrates example architecture of an example PID VOC sensor, in accordance with an example embodiment of the present disclosure.

Referring now to FIG. 4A, a cross-section of an example PID VOC sensor 400 is provided. As shown in FIG. 4A, the example PID VOC sensor 400 includes a PID detecting region 404 wherein a first interdigital pole 202 and a second interdigital pole 206 are disposed. Further contained in the PID detecting region 404 is a plurality of ionized molecules 416 and a plurality of non-ionized molecules 424. From one side of the PID VOC sensor 400, input gas 414 is diffused into the PID detecting region 404. From the opposite side of the PID VOC sensor 400, an ionization source 402 is disposed and directed to the PID detecting region 404 to ionize molecules from the input gas 414. In addition, a separation voltage source 406 is electrically connected to the first interdigital pole 202. A switch 408 is electrically connected to the second interdigital pole 206, providing selectable electrical connectivity to a compensation voltage source 410 and a processing device 412.

As depicted in FIG. 4A, the example PID VOC sensor 400 includes a PID detecting region 404. As described herein, the PID detecting region 404 is utilized to ionize, separate, and detect targeted VOC molecules. The PID detecting region 404 depicted in FIG. 4 includes an opening allowing input gas 414 to diffuse into the PID detecting region 404. The input gas 414 may be any gas, vapor, or other similar matter in which the detection of VOCs is desired. The input gas 414 may be received from the surrounding environment, from a person's or animal's breath, from hazardous areas, from a contained gas source, from fumes emanating from a fuel, solvent, or other object, the environment in an industrial or chemical plant, and/or from other similar sources of gas which may contain VOCs. In order for detection to occur, the gas must diffuse into the PID detecting region 404 for ionization, separation, and detection.

As further depicted in FIG. 4A, the example PID VOC sensor 400 includes an ionization source 402 which is directed at the PID detecting region 404 and interacts with molecules of the input gas 414. An ionization source 402, may be any component, device, or substance configured to break the chemical bonds of VOCs such that ionized molecules result. The ionization phase of the detection process is characterized by the enabling of the ionization source 402 and the interaction of the emitted ionization source 402 photons with the input gas 414 molecules. A VOC molecule will be ionized only if the ionization potential of the particular VOC molecule is less that the energy emitted by the ionization source 402. In some embodiments, a UV lamp may be used as an ionization source 402. A UV lamp may emit photons of different energy based on the gas within the photon lamp. For example, an ionization lamp may contain Krypton, Xenon, Argon, etc. Each of these sources, when heated up, may output photons of different energy, thus ionizing a different range of potentially detectable VOCs. The ionization source 402 may be disabled during the detection phase, allowing the target ions to move toward the second interdigital pole 206 for counting without further ionization of molecules. By disabling the ionization source 402 during the detection phase, the life of the ionization source 402 may be prolonged.

As the input gas 414 enters the PID detecting region 404 and interacts with the photons emitted from the ionization source 402, a plurality of ionized molecules 416 are generated. Once molecules are ionized, the ionized molecules 416 carry an electric charge. As such, the molecules may become responsive to an electric field. In addition, ionized molecules may be de-ionized when they contact an electric source, such as an electrode. Further, ionized molecules may be detected when contacting an electric probe connected to a processing device.

As further depicted in FIG. 4A, the example PID VOC sensor 400 includes a separation voltage source 406 electrically connected to the first interdigital pole 202. As described in relation to FIG. 2, the applied separation voltage may be an asymmetric waveform comprising a repeating pattern, including a high voltage component lasting for a short period of time and a lower voltage component of opposing polarity lasting for a longer period of time. The separation voltage has the effect of separating ionized molecules based on the ratio of the molecule's mobility in a high electric field (V h) to the molecule's mobility in a low electric field ($V_1$). Unequal mobilities will cause the ionized molecules to drift toward one interdigital pole or the other.

As further depicted in FIG. 4A, the example PID VOC sensor 400 includes a switch 408. A switch 408 may be any mechanical, electromechanical, analog, or electrical device that allows an electrical connection between the second interdigital pole 206 and alternatively between the compensation voltage source 410 and the processing device 412. The switch 408, in some embodiments, may comprise a single pole double throw switch wherein the single input (e.g., single input connector) is electrically connected to the second interdigital pole 206 and one output (e.g., first output connector) is electrically connected to the compensation voltage source 410 while the other output (e.g., second output connector) is electrically connected to the processing device 412. The switch 408 may be controlled through electrical communication by the processing device 412 or another similar device capable of electrical communication.

In some embodiments, the switch 408 may be switched by receipt of a change in electrical signal (e.g., a change in voltage level) or by an electrical pulse. In some embodiments, the switch 408 state may be switched in coordination with the enabling/disabling of the ionization source 402, as further described in relation to FIG. 7.

As further depicted in FIG. 4A, the example PID VOC sensor 400 further includes a compensation voltage source 410 electrically connected to an output of the switch 408. The switch 408 may be configured to connect the compensation voltage source 410 to the second interdigital pole 206 during the ionization and compensation phases. In an instance in which the switch 408 is configured such that an electrical connection is made between the compensation voltage source 410 and the second interdigital pole 206, a compensation voltage may be provided to the second interdigital pole 206. A compensation voltage may be any voltage applied to the second interdigital pole 206 to compensate for the drift of a target ion toward either interdigital pole (e.g., first interdigital pole 202 and second interdigital pole 206). A compensation voltage may depend on a number of factors, including the mobility of the VOC ion of interest, the separation voltage, the pulse width of the compensation voltage waveform, the space between the electrodes, and other similar factors.

As one example, in general, a benzene VOC may require a lower compensation voltage, for example, between +2 volts and +5 volts. Thus, if a benzene ion when subjected to the separation voltage drifts toward the second interdigital pole 206, the applied compensation voltage produced by the compensation voltage source 410 may force the benzene ion away from the second interdigital pole such that the net drift of the benzene ion is nullified and the target benzene ion remains in the electric field region 210 while the separation voltage oscillates the electric field in the electric field region 210. Other targeted VOC ions may require a different compensation voltage. For example, an acetone ion may require a higher compensation voltage, for example, between +13 and +17 volts, to keep the targeted acetone ions in the electric field region 210. In some embodiments, the compensation voltage source 410 may update or change the compensation voltage to detect other VOCs of interest during operation. In some embodiments, the compensation voltage source 410 may coordinate these updates with the enabling/disabling of the ionization source 402 and/or the switching of the switch 408.

As further depicted in FIG. 4A, the example PID VOC sensor 400 further includes a processing device 412 electrically connected to an output of the switch 408. The processing device 412 may be any device capable of detecting a change in voltage based on the presence of ions on the connected electrode (e.g., second interdigital pole 206). In some embodiments, the processing device 412 may be a high speed signal processing circuit. The processing device 412 may be substantially connected during the detection phase of the VOC detection process. In addition to connecting the processing device 412 to the second interdigital pole 206, the detection phase is defined by a constant voltage set on the first interdigital pole 202 (e.g., first constant DC voltage) and the second interdigital pole 206 (e.g., second constant DC voltage). In some embodiments, the constant voltage applied to the interdigital poles may be between 30 volts and 200 volts. Applying a constant voltage to the poles forces the ionized molecules to drift toward the second interdigital pole 206 for detection. The processing device 412 may determine a VOC value which, in some embodiments, may represent the presence of the targeted VOC. In some embodiments, the VOC value may represent the concentrations of a target VOC based on the change in voltage detected on the second interdigital pole 206. In some embodiments, the detected signal will peak within a short time interval, for example 0.1 milliseconds to 2 milliseconds after the constant current on the interdigital poles has been applied.

In some embodiments, the processing device may configure the components of the PID VOC sensor 400. For example, the processing device 412 may control the voltage output of the separation voltage source 406, the enabling/disabling of the ionization source 402, the switching of the switch 408, the adjustment of the DC compensation voltage from the compensation voltage source 410, and/or other similar configurable elements. In some embodiments, these configuration commands may be issued through wireless and/or wired communication between the components.

Figure 4B:
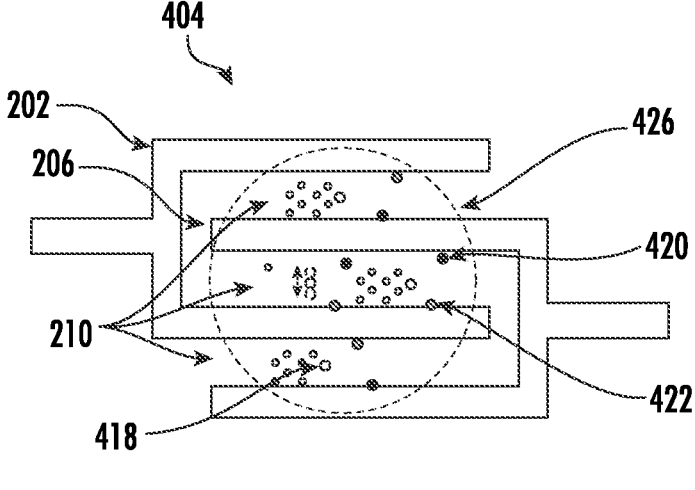
FIG. 4B illustrates a close-up view of the interdigital pole conducting elements of an example PID VOC sensor, in accordance with an example embodiment of the present disclosure.

Referring now to FIG. 4B, a close-up view of the PID detecting region 404 is provided. The PID detecting region 404 may operate in three separate phases. First, the PID detecting region 404 operates in an ionization phase. During the ionization phase, the ionization source 402 is enabled. The ionization region 426 represents an area in which molecules present in the input gas 414 may interact with the ionization source and become ionized. The PID detecting region 404 may also operate in a separation phase. The separation phrase, in some embodiments, substantially overlaps with the ionization phase. The separation phase is characterized by the first interdigital pole 202 connected to a separation voltage source 406 and the second interdigital pole 206 connected via the switch 408 to the compensation voltage source 410. During the separation phrase, non-targeted ions (e.g., ions 420, 422) drift toward one of the two interdigital poles based on the ratio of the mobility of the ion in the presence of a high electric field to the mobility of the ion in the presence of a low electric field ($K_h/K_1$). However, the compensation voltage source 410 is configured to compensate the drift of targeted ions (e.g., ion 418) during the separation phase, such that the targeted ions remain in the electric field region 210 during the separation phase. In general, the ionization source 402 is disabled sometime before the start of the detection phase. The detection phase is characterized by the switch 408, electrically connecting the second interdigital pole to the processing device 412, as well as the application of a constant DC voltage to the first interdigital pole 202 and the second interdigital pole 206, forcing the targeted ions toward the second interdigital pole 206. The processing device 412 may then determine a VOC value representing the presence and concentration of the targeted VOC based on the change in voltage on the second interdigital pole 206 due to contact with the now drifting targeted ions (e.g., ion 418).

Figure 5:
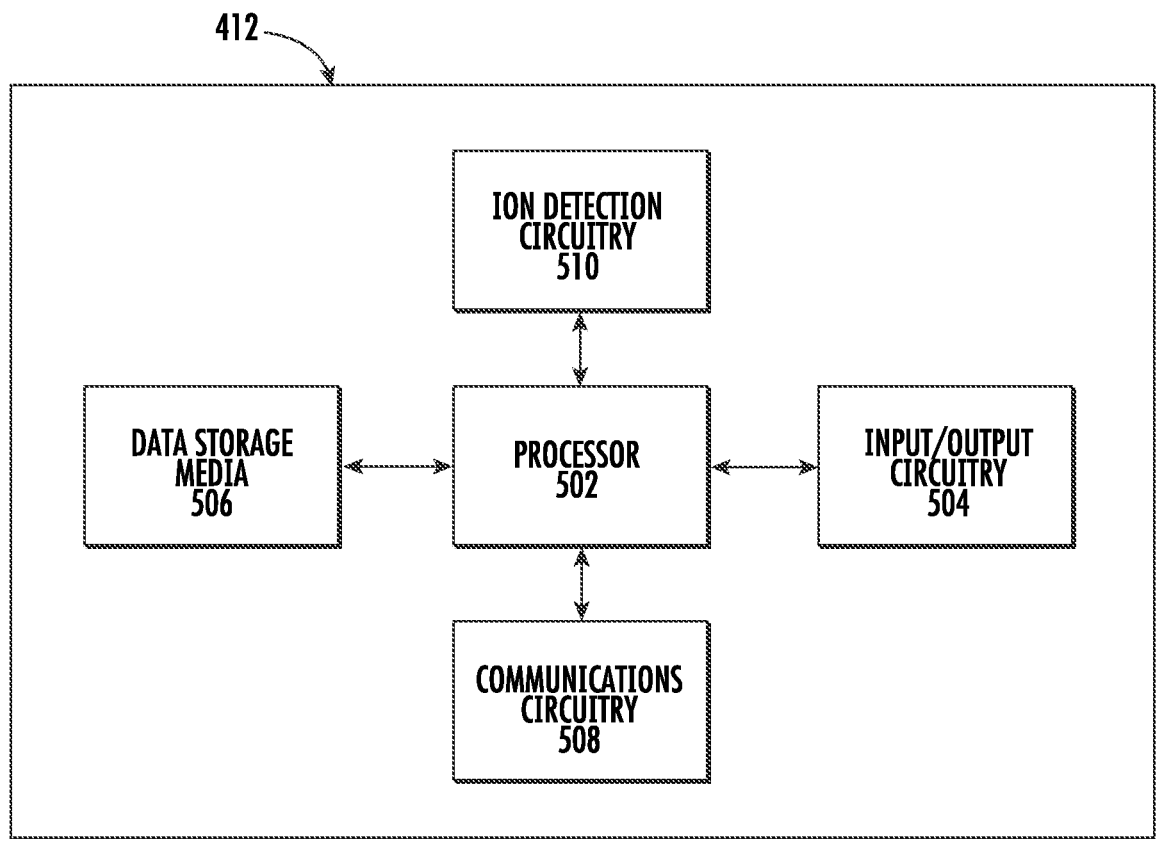
FIG. 5 illustrates an example block diagram showing example components of a processing device, in accordance with an example embodiment of the present disclosure.

FIG. 5 illustrates an example processing device 412 in accordance with at least some example embodiments of the present disclosure. The processing device 412 includes processor 502, input/output circuitry 504, data storage media 506, communications circuitry 508, and ion detection circuitry 510. In some embodiments, the processing device 412 is configured, using one or more of the sets of circuitry 502, 504, 506, 508, and/or 510, to execute and perform the operations described herein.

Although components are described with respect to functional limitations, it should be understood that the particular implementations necessarily include the use of particular computing hardware. It should also be understood that in some embodiments certain of the components described herein include similar or common hardware. For example, two sets of circuitry may both leverage use of the same processor(s), network interface(s), storage medium(s), and/or the like, to perform their associated functions, such that duplicate hardware is not required for each set of circuitry. The user of the term "circuitry" as used herein with respect to components of the apparatuses described herein should therefore be understood to include particular hardware configured to perform the functions associated with the particular circuitry as described herein.

Particularly, the term "circuitry" should be understood broadly to include hardware and, in some embodiments, software for configuring the hardware. For example, in some embodiments, "circuitry" includes processing circuitry, storage media, network interfaces, input/output devices, and/or the like. Alternatively or additionally, in some embodiments, other elements of the processing device 412 provide or supplement the functionality of other particular sets of circuitry. For example, the processor 502 in some embodiments provides processing functionality to any of the sets of circuitry, the data storage media 506 provides storage functionality to any of the sets of circuitry, the communications circuitry 508 provides network interface functionality to any of the sets of circuitry, and/or the like.

In some embodiments, the processor 502 (and/or co-processor or any other processing circuitry assisting or otherwise associated with the processor) is/are in communication with the data storage media 506 via a bus for passing information among components of the processing device 412. In some embodiments, for example, the data storage media 506 is non-transitory and may include, for example, one or more volatile and/or non-volatile memories. In other words, for example, the data storage media 506 in some embodiments includes or embodies an electronic storage device (e.g., a computer readable storage medium). In some embodiments, the data storage media 506 is configured to store information, data, content, applications, instructions, or the like, for enabling the processing device 412 to carry out various functions in accordance with example embodiments of the present disclosure.

The processor 502 may be embodied in a number of different ways. For example, in some example embodiments, the processor 502 includes one or more processing devices configured to perform independently. Additionally or alternatively, in some embodiments, the processor 502 includes one or more processor(s) configured in tandem via a bus to enable independent execution of instructions, pipelining, and/or multithreading. The use of the terms "processor" and "processing circuitry" should be understood to include a single core processor, a multi-core processor, multiple processors internal to the processing device 412, and/or one or more remote or "cloud" processor(s) external to the processing device 412.

In an example embodiment, the processor 502 is configured to execute instructions stored in the data storage media 506 or otherwise accessible to the processor. Alternatively or additionally, the processor 502 in some embodiments is configured to execute hard-coded functionality. As such, whether configured by hardware or software methods, or by a combination thereof, the processor 502 represents an entity (e.g., physically embodied in circuitry) capable of performing operations according to an embodiment of the present disclosure while configured accordingly. Alternatively or additionally, as another example in some example embodiments, when the processor 502 is embodied as an executor of software instructions, the instructions specifically configure the processor 502 to perform the algorithms embodied in the specific operations described herein when such instructions are executed.

As one particular example embodiment, the processor 502 is configured to perform various operations associated with the detection of VOCs in a gas. In some embodiments, the processor 502 includes hardware, software, firmware, and/or a combination thereof, that executes an ionization phase comprising exposing the gas to an ionization device (e.g., ionization source 102) creating a plurality of ionized gas molecules. Additionally or alternatively, in some embodiments, the processor 502 includes hardware, software, firmware, and/or a combination thereof, that executes a separation phase comprising supplying a separation voltage to a first interdigital pole 202 disposed within the detecting region (e.g., PID detecting region 404) and electrically connected to a separation voltage source 406 and supplying a compensation voltage to a second interdigital pole 206 disposed within the detecting region and electrically connected to a compensation voltage source 410 through a switch 408. Additionally or alternatively, in some embodiments, the processor 502 includes hardware, software, firmware, and/or a combination thereof, that disables the ionization device upon completion of the ionization phase. Additionally or alternatively, in some embodiments, the processor 502 includes hardware, software, firmware, and/or a combination thereof, that executes a detection phase comprising: switching the switch 408 to electrically connect the second interdigital pole 206 to a processing device 412; supplying a first direct current voltage to the first interdigital pole 202 and supplying a second direct current voltage to the second interdigital pole 206; and determining a VOC value representative of a number of volatile organic compounds in the gas based at least in part on a number of ionized gas molecules that contact the second interdigital pole 206 while the second interdigital pole 206 is electrically connected to the processing device 412.

In some embodiments, the processing device 412 includes input/output circuitry 504 that provides output to the user and, in some embodiments, to receive an indication of a user input. In some embodiments, the input/output circuitry 504 is in communication with the processor 502 to provide such functionality. The input/output circuitry 504 may comprise one or more user interface(s) (e.g., user interface) and in some embodiments includes a display that comprises the interface(s) rendered as a web user interface, an application user interface, a user device, a backend system, or the like. The processor 502 and/or input/output circuitry 504 comprising the processor may be configured to control one or more functions of one or more user interface elements through computer program instructions (e.g., software and/or firmware) stored on a memory accessible to the processor (e.g., data storage media 506, and/or the like). In some embodiments, the input/output circuitry 504 includes or utilizes a user-facing application to provide input/output functionality to a client device and/or other display associated with a user.

In some embodiments, the processing device 412 includes communications circuitry 508. The communications circuitry 508 includes any means such as a device or circuitry embodied in either hardware or a combination of hardware and software that is configured to receive and/or transmit data from/to a network and/or any other device, circuitry, or module in communication with the processing device 412. In this regard, the communications circuitry 508 includes, for example in some embodiments, a network interface for enabling communications with a wired or wireless communications network. Additionally or alternatively in some embodiments, the communications circuitry 508 includes one or more network interface card(s), antenna(s), bus(es), switch(es), router(s), modem(s), and supporting hardware, firmware, and/or software, or any other device suitable for enabling communications via one or more communications network(s). Additionally or alternatively, the communications circuitry 508 includes circuitry for interacting with the antenna(s) and/or other hardware or software to cause transmission of signals via the antenna(s) or to handle receipt of signals received via the antenna(s). In some embodiments, the communications circuitry 508 enables transmission to and/or receipt of data from a client device in communication with the processing device 412.

The ion detection circuitry 510 includes hardware, software, firmware, and/or a combination thereof, that supports various functionality associated with detecting volatile organic compounds (VOCs) in an input gas 414 diffused into a detecting region (e.g., PID detecting region 404). For example, in some embodiments, the ion detection circuitry 510 includes hardware, software, firmware, and/or a combination thereof to execute an ionization phase comprising exposing the gas to an ionization source 402 creating a plurality of ionized gas molecules. Additionally or alternatively, in some embodiments, the ion detection circuitry 510 includes hardware, software, firmware, and/or a combination thereof, that executes a separation phase comprising supplying a separation voltage to a first interdigital pole 202 disposed within the detecting region and electrically connected to a separation voltage source 406, and supplying a compensation voltage to a second interdigital pole 206 disposed within the detecting region and electrically connected to a compensation voltage source 410 through a switch 408. Additionally or alternatively, in some embodiments, the ion detection circuitry 510 includes hardware, software, firmware, and/or a combination thereof, that disables the ionization source 402 upon completion of the ionization phase. Additionally, or alternatively the ion detection circuitry 510 includes hardware, software, firmware, and/or a combination thereof, that executes a detection phase comprising switching the switch 408 to electrically connect the second interdigital pole 206 to a processing device 412, supplying a first direct current voltage to the first interdigital pole 202 and supplying a second direct current voltage to the second interdigital pole 206, and determining a VOC value representative of the number of volatile organic compounds in the input gas 414 based at least in part on the number of ionized gas molecules that contact the second interdigital pole 206 while the second interdigital pole 206 is electrically connected to the processing device 412. In some embodiments, the ion detection circuitry 510 includes a separate processor, specially configured field programmable gate array (FPGA), or a specially programmed application specific integrated circuit (ASIC).

Additionally or alternatively, in some embodiments, one or more of the sets of circuitry 502-510 are combinable. Additionally or alternatively, in some embodiments, one or more of the sets of circuitry perform some or all of the functionality described associated with another component. For example, in some embodiments, one or more sets of circuitry 502-510 are combined into a single module embodied in hardware, software, firmware, and/or a combination thereof. Similarly, in some embodiments, one or more of the sets of circuitry, for example ion detection circuitry 510, is/are combined such that the processor 502 performs one or more of the operations described above with respect to each of these circuitry individually.

Figure 6:
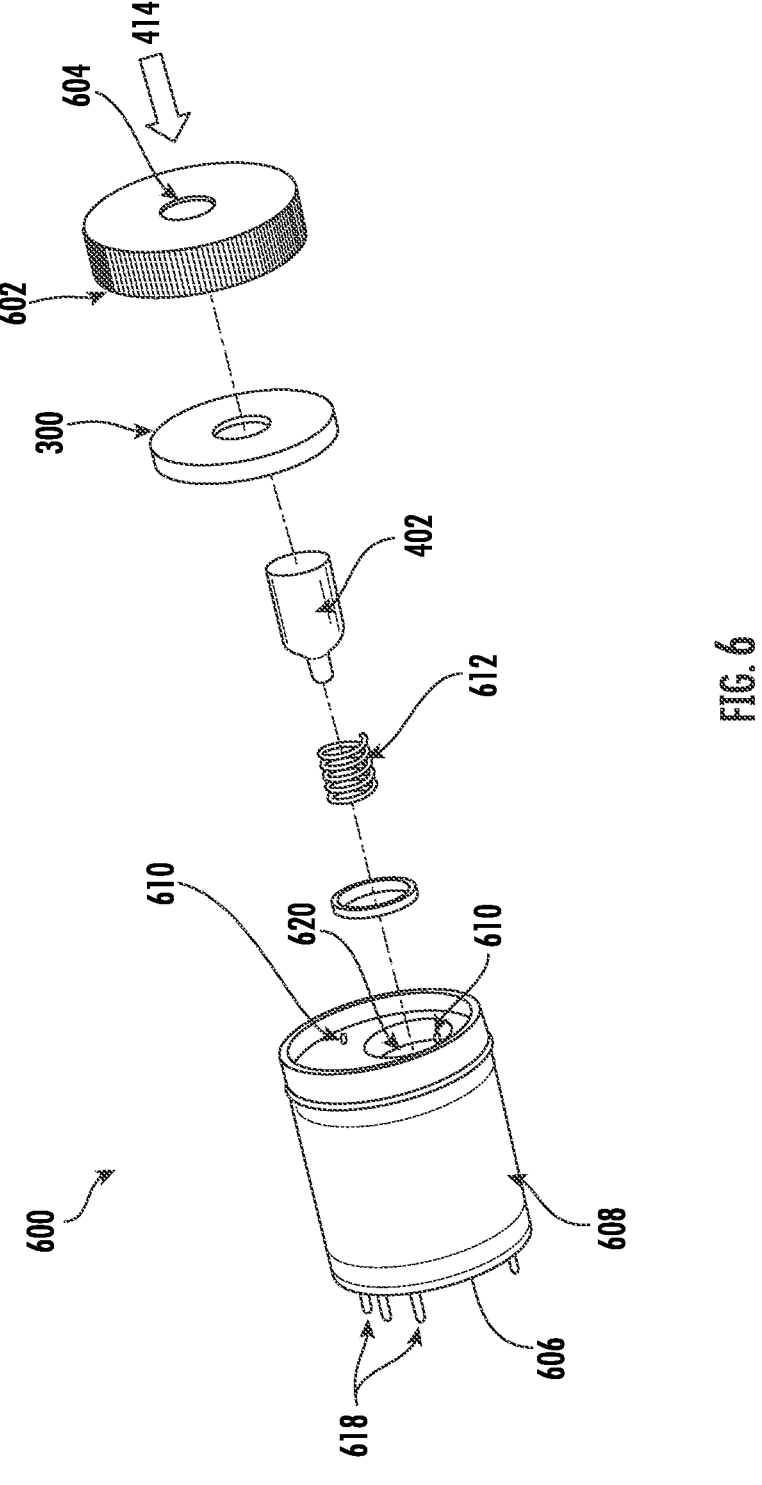
FIG. 6 illustrates an example PID VOC sensor housing and internal components, in accordance with an example embodiment of the present disclosure.

Referring now to FIG. 6, an example PID VOC sensor housing 600 is provided. As shown in FIG. 6, the example PID VOC sensor housing 600 includes a housing base 606 comprising a plurality of electrical connectors 618. In some embodiments, the processing device 412 may be attached to the housing base 606. In some embodiments, the processing device may be shaped to fit the cross-sectional shape of the PID VOC sensor housing 600 and/or the housing base 606 may comprise the processing device 412. In some embodiments, the plurality of electrical connectors 618 (e.g., first electrical connector and second electrical connector) electrically connect to one or more pogo pin connectors 610, extending beyond the side of the housing base 606 opposite the plurality of electrical connectors 618, passing through the electrical connector opening 324 (as seen in FIG. 3) in the interdigital pole bottom cover 308 (as seen in FIG. 3), and contacting the first conducting pad 212 and the second conducting pad 214 of the interdigital pole component 300.

The example PID VOC sensor housing 600, as shown in FIG. 6, further includes a housing wall 608. The housing wall 608 extends from the base and forms an enclosed perimeter, defining an interior cavity 620.

The example PID VOC sensor housing 600 further includes an ionization source contact coil 612 positioned between the ionization source 402 and an electrical conductor (not shown) on the housing base 606 in the interior cavity 620 of the PID VOC sensor housing 600. The ionization source contact coil 612 provides electrical connectivity to the ionization source 402 and compressive force against the ionization source 402, securing the ionization source 402 in a position against the interdigital pole component 300. The position of the ionization source 402 enables the ionization source 402 to interact with the input gas 414 in the interdigital pole component 300 through the interdigital poles exposure window 322 (as seen in FIG. 3).

As further illustrated in FIG. 6, the interdigital pole component 300 is also disposed in the interior cavity 620 of the PID VOC sensor housing 600 against the ionization source 402 and secured into place by the housing cap 602. In some embodiments, the housing cap 602 may be attached to the housing wall 608, substantially sealing the interior cavity 620. The housing cap 602 further comprises a cap vent 604 allowing input gas 414 to enter into the PID VOC sensor device and into the PID detecting region 404 (as seen in FIG. 4) of the interdigital pole component 300.

Figure 7:
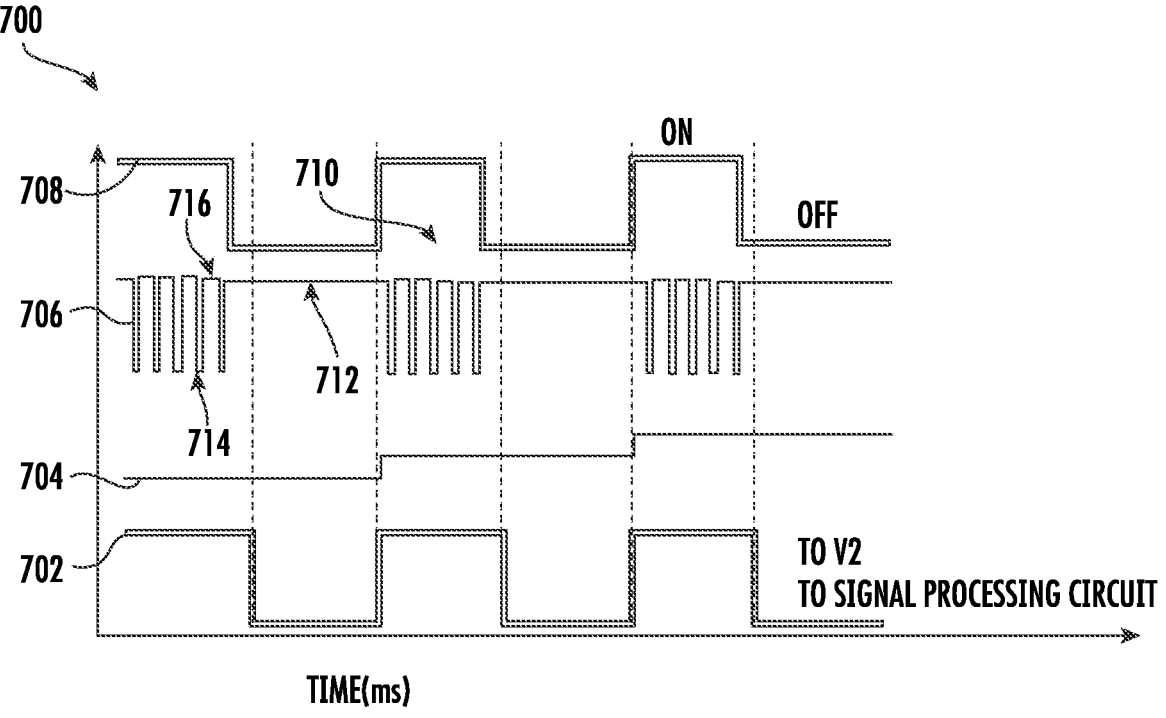
FIG. 7 illustrates an example PID VOC sensor signal sequence, in accordance with an example embodiment of the present disclosure.

Referring now to FIG. 7, an example PID VOC sensor signal sequence 700 is shown. Starting from the bottom, a compensation voltage switch output signal 702 is shown. As shown in FIG. 7, when the compensation voltage switch output signal 702 is high, the PID VOC sensor 400 switch 408 switches the output to electrically connect the second interdigital pole 206 to the compensation voltage source 410. While connected to the compensation voltage source 410, the PID VOC sensor 400 is operating in the ionization and/or separation phase, in which non-targeted ionized ions drift toward one of the interdigital poles, while the targeted ions remain in the electric field region 210. As further shown in FIG. 7, when the compensation voltage switch output signal 702 is low, the PID VOC sensor 400 switch 408 switches the output to electrically connect the second interdigital pole 206 to the processing device 412. While connected to the processing device 412, the PID VOC sensor 400 is operating in the detection phase, in which a constant DC voltage is applied to both interdigital poles and the targeted ions drift to contact the second interdigital pole 206. Once in contact with the second interdigital pole 206, the processing device may determine a VOC value by converting the change in voltage to count and/or concentration of the targeted VOCs.

A compensation voltage source signal 704 is further illustrated in FIG. 7. In some embodiments, a compensation voltage source 410 may apply a compensation voltage to the second interdigital pole 206 during the separation phase. The compensation voltage may be a DC voltage configured based on the mobility of the VOC ion of interest in the applied electric field. The compensation voltage may compensate for the drift of a target ion toward either interdigital pole (e.g., first interdigital pole 202 and second interdigital pole 206). By applying a compensation voltage, the targeted ions will remain in the electric field region 210 during the separation phase, while other ionized molecules will drift toward one of the interdigital poles. As shown in the example compensation voltage source signal 704 of FIG. 7, the compensation voltage may be adjusted between detection cycles. For example, a compensation voltage may be selected to target a first VOC. The selected compensation voltage is applied to the second interdigital pole 206 during the ionization and separation phases, separating the ionized molecules of the first VOC from other ionized molecules. The ionized molecules of the first VOC are then detected during the detection phase. The compensation voltage may then be adjusted to target a second VOC. The PID VOC sensor 400 will then cycle through the ionization, separation, and detection phases with the new compensation voltage, detecting the presence and concentration of the second VOC. This process can continue based on the number and type of VOCs detected.

A separation voltage signal 706 is further illustrated in FIG. 7. As shown in FIG. 7, during the separation phase of VOC detection, the applied separation voltage is an asymmetric waveform comprising a repeating pattern (e.g., 710), including a high voltage component (e.g., 714) lasting for a short period of time and a lower voltage component (e.g., 716) of opposing polarity lasting for a longer period of time. The separation voltage has the effect of separating ionized molecules based on the molecule's mobility, causing the ionized molecules to drift toward one interdigital pole or the other. Adjustments may be made to the separation voltage and the compensation voltage to target a specific VOC based on the mobility of the ionized molecules of the VOC. As further illustrated in FIG. 7, during the detection phase, a direct current voltage (e.g., 712) is applied to the first interdigital pole 202. Applying a constant voltage may cause the targeted ions remaining in the electric field region 210 to drift toward the second interdigital pole 206 for detection by the processing device 412.

An ionization source input voltage signal 708 is further illustrated in FIG. 7. The ionization source input voltage signal 708 illustrates an example voltage provided to the ionization source 402 during the operation of the PID VOC sensor 400. As shown in FIG. 7, when the ionization source input voltage signal 708 is high, the ionization source 402 is enabled. Alternatively, when the ionization source input voltage signal 708 is low, the ionization source is disabled. The ionization phase occurs while the ionization source 402 is enabled. During this phase, the ionization source 402 (e.g., UV lamp) interacts with the ions in the PID detecting region 404. This interaction ionizes VOC molecules contained in the input gas 414. In the example ionization source input voltage signal 708 shown in FIG. 7, the ionization source 402 is turned off before the separation phase concludes. Shutting the ionization source 402 off before the conclusion of the separation phase allows the ionized molecules to finish drifting during the last cycle of the separation phase. Shutting the ionization source 402 off before the conclusion of the separation phase also ensures molecules are no longer being ionized during the detection phase. Enabling and disabling the ionization source 402 during the detection of VOCs, allows the ionization, separation, and detection phases to occur within the same physical space (e.g., PID detecting region 404. Further, enabling and disabling the ionization source 402 may prolong the life of the ionization source 402, particularly, in an instance in which the ionization source 402 is a UV lamp.

Figure 8:
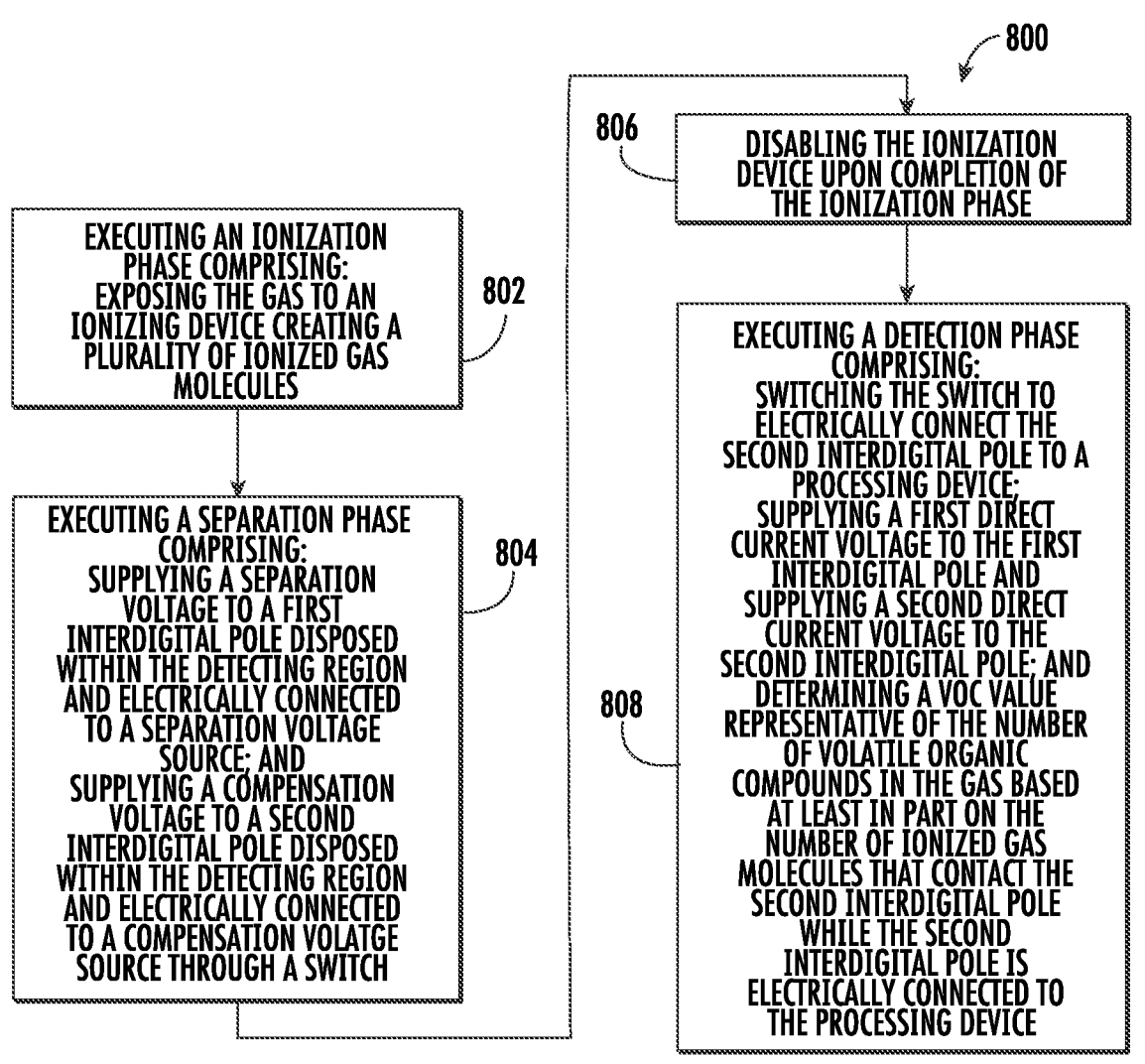
FIG. 8 depicts a flowchart illustrating example operations performed by a processing device to detect VOCs in a PID VOC sensor, in accordance with an example embodiment of the present disclosure.

Referring now to FIG. 8, an example method for detecting VOCs in a gas (e.g., input gas 414) diffused into a detecting region (e.g., PID detecting region 404) of a VOC sensor (e.g., PID VOC sensor 400) is illustrated. The example method 800 starts at block 802 when a processing device (e.g., processing device 412) executes an ionization phase comprising exposing the gas to an ionization source 402 creating a plurality of ionized gas molecules. During the ionization phase, the ionization source 402 is enabled. In some embodiments, the processing device may enable the ionization source 402. The processing device may control the power output to the ionization source 402 through wired and/or wireless communication to a control device, for example, a switch. The processing device may signal a control device to enable power by sending a pulse or by changing an input voltage, for example, from a '0' to a '1.' Further, a processing device may communicate with the control device through a synchronous protocol, such as I2C.

At block 804, the processing device executes a separation phase comprising supplying a separation voltage to a first interdigital pole (e.g., first interdigital pole 202) disposed within the detecting region (e.g., PID detecting region 404) and electrically connected to a separation voltage source (e.g., separation voltage source 406) and supplying a compensation voltage to a second interdigital pole (e.g., second interdigital pole 206) disposed within the detecting region and electrically connected to a compensation voltage source (e.g., compensation voltage source 410) through a switch (e.g., switch 408). As previously described, the separation phase is characterized by a first set of interdigital poles connected to a separation voltage source delivering an asymmetric waveform comprising a repeating pattern (e.g., 710), including a high voltage component (e.g., 714) lasting for a short period of time and a lower voltage component (e.g., 716) of opposing polarity lasting for a longer period of time, in an effort to separate targeted ions from other ionized compounds. The processing device may configure the output of the separation voltage source directly such that the voltage is provided as described above. In some embodiments, the separation voltage source may be attached to a switching mechanism such that the processing device enables the oscillating asymmetric waveform during the separation phase and enables a separate DC voltage source during the detection phase.

At block 806, the processing device disables the ionization device (e.g., ionization source 402) upon completion of the ionization phase. The processing device through communication mechanisms described with reference to block 802 may disable the ionization source previous to the conclusion of the separation phase, allowing the separation phase to conclude and ensuring molecules are no longer being ionized during the detection phase.

At block 808, the processing device executes a detection phase comprising switching the switch to electrically connect the second interdigital pole 206 to the processing device, supplying a first direct current voltage to the first interdigital pole 202 and supplying a second direct current voltage to the second interdigital pole 206, and determining a VOC value representative of a number of volatile organic compounds in the gas based at least in part on a number of ionized gas molecules that contact the second interdigital pole 206 while the second interdigital pole 206 is electrically connected to the processing device. The detection phase is characterized by applying a DC voltage to both the interdigital poles and electrically connecting the processing device to at least one of the interdigital poles. The processing device may configure the switch (e.g., switch 408) to electrically connect at least one of the interdigital poles to the processing device. The processing device may further provide a constant DC voltage to the set of interdigital poles connected to the separation voltage source. In some embodiments, the processing device may directly configure the separation voltage source to output a constant DC voltage. In some embodiments, the processing device may configure a switch to switch between the separation voltage source and a constant DC voltage source once the separation phase has completed. Similarly, the processing device may enable a constant DC voltage on the interdigital poles connected to the processing device through a switching mechanism, or by providing the DC voltage source directly.

The processing device may further determine a VOC value based on the number of detected VOCs. In some embodiments, the VOC value may represent the presence of VOCs. For example, if the increase in voltage due to the presence of detected ions is greater than a threshold, the VOC value indicates that the VOC is present in the gas, otherwise, the VOC value indicates that no VOCs are present. In some embodiments, the VOC value may represent the total number of VOCs detected in the given time range based on the detected increase in voltage due to the detected ionized VOCs. In some embodiments, the VOC value may represent the number of detected VOCs over a range of compensate voltages. For example, the PID VOC sensor 400 may cycle through a range of compensate voltages, recording the increase in voltage due to the detected ions at each incremental compensate voltage. A VOC value may be a curve and/or graph representing the change in VOCs based on the compensate voltage.

Many modifications and other embodiments set forth herein will come to mind to one skilled in the art to which these inventions pertain having the benefit of teachings presented in the foregoing descriptions and the associated drawings. Although the figures only show certain components of the apparatus and systems described herein, it is understood that various other components may be used in conjunction with the system. Therefore, it is to be understood that the inventions are not to be limited to the specific embodiments disclosed and that modifications and other embodiments are intended to be included within the scope of the appended claims. Moreover, the steps in the method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure.

Use of broader terms such as "comprises," "includes," and "having" should be understood to provide support for narrower terms such as "consisting of," "consisting essentially of," and "comprised substantially of" Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

What is claimed is:

1. An apparatus for detecting volatile organic compounds (VOCs) in a gas, the apparatus comprising:
   a processing device; and
   a detecting region comprising:
      a first interdigital pole disposed within the detecting region and electrically connected to a separation voltage source;
      a second interdigital pole disposed within the detecting region and electrically connected to a switch; and
      an ionization device configured to interact with the gas within the detecting region creating a plurality of ionized gas molecules;
   wherein the switch alternates a connection of the second interdigital pole between a compensation voltage source and the processing device; and
   wherein the processing device determines a VOC value representative of a number of volatile organic compounds in the gas based at least in part on a number of ionized gas molecules that contact the second interdigital pole while the second interdigital pole is electrically connected to the processing device.

2. The apparatus of claim 1, further comprising a housing comprising:
   a base, wherein the processing device is attached to the housing at or near the base;
   a housing wall protruding from the base forming an enclosed perimeter around an interior cavity and defining an opening opposite the base,
      wherein the switch is positioned in the interior cavity and attached to the housing, and
      wherein the ionization device is disposed proximate the base and directed toward the opening;
   a cap detachably connected to the housing wall, substantially covering the opening and further comprising a vent, wherein the gas enters the housing through the vent,
      wherein the detecting region is positioned inside the interior cavity of the housing between the vent in the cap of the housing and the ionization device,
   a first electrical connector disposed on the exterior of the housing and providing electrical connectivity from the separation voltage source to the interior cavity of the housing; and a second electrical connector disposed on the exterior of the housing and providing electrical connectivity from the compensation voltage source to the interior cavity of the housing;

wherein the first interdigital pole of the detecting region is electrically connected to the first electrical connector, and wherein the switch is positioned inside the interior cavity of the housing and alternates an electrical connection from the second electrical connector and the processing device to the second interdigital pole of the detecting region.

3. The apparatus of claim 1, wherein the first and second interdigital poles each comprise a plurality of comb-like conducting prongs, wherein the plurality of comb-like conducting prongs of the first interdigital pole are directed toward the plurality of comb-like conducting prongs of the second interdigital pole, and wherein the second interdigital pole is offset from the first interdigital pole such that the plurality of comb-like conducting prongs of the first interdigital pole occupy a space between the plurality of comb-like conducting prongs of the second interdigital pole.

4. The apparatus of claim 1, wherein the apparatus operates in at least three time phases, an ionization phase wherein gas molecules of the gas are exposed to the ionization device, a separation phase wherein a separation voltage is applied to the first interdigital pole, and a detection phase wherein the switch is positioned to electrically connect the second interdigital pole to the processing device.

5. The apparatus of claim 4, wherein the ionization phase and the separation phase substantially overlap.

6. The apparatus of claim 1, wherein the ionization device is an ultraviolet lamp projecting UV light into the detecting region, and gas molecules with an ionization potential lower than ionization energy of the UV light are ionized.

7. The apparatus of claim 6, wherein the ultraviolet lamp is substantially on during the ionization phase and substantially off during the detection phase.

8. The apparatus of claim 1, wherein the switch is a single pole double throw switch having an input side with a single input connector and an output side having a first output connector and a second output connector, and wherein the single input connector is electrically connected to the second interdigital pole, the first output connector is electrically connected to the compensation voltage source, and the second output connector is electrically connected to the processing device.

9. The apparatus of claim 4, wherein the detection phase is defined by:

the switch providing an electrical connection between the second interdigital pole and the processing device;

a first constant DC voltage is supplied to the first interdigital pole and a second constant DC voltage is supplied to the second interdigital pole; and the ionization device is disabled.

10. The apparatus of claim 4, wherein the separation voltage source provides an alternating current to the first interdigital pole during the separation phase and the separation voltage source otherwise supplies a constant direct current voltage to the first interdigital pole.

11. The apparatus of claim 1, wherein the compensation voltage source is a direct current voltage.

12. A method for detecting volatile organic compounds (VOCs) in a gas diffused into a detecting region of a VOC sensor, the method comprising:

executing an ionization phase comprising:

exposing the gas to an ionization device creating a plurality of ionized gas molecules;

executing a separation phase comprising:

supplying a separation voltage to a first interdigital pole disposed within the detecting region and electrically connected to a separation voltage source; and supplying a compensation voltage to a second interdigital pole disposed within the detecting region and electrically connected to a compensation voltage source through a switch;

disabling the ionization device upon completion of the ionization phase; and executing a detection phase comprising:

switching the switch to electrically connect the second interdigital pole to a processing device;

supplying a first direct current voltage to the first interdigital pole and supplying a second direct current voltage to the second interdigital pole; and determining a VOC value representative of a number of volatile organic compounds in the gas based at least in part on a number of ionized gas molecules that contact the second interdigital pole while the second interdigital pole is electrically connected to the processing device.

13. The method of claim 12, wherein the first and second interdigital poles each comprise a plurality of comb-like conducting prongs, wherein the plurality of comb-like conducting prongs of the first interdigital pole are directed toward the plurality of comb-like conducting prongs of the second interdigital pole, and wherein the second interdigital pole is offset from the first interdigital pole such that the plurality of comb-like conducting prongs of the first interdigital pole occupy a space between the plurality of comb-like conducting prongs of the second interdigital pole.

14. The method of claim 12, wherein the ionization phase and the separation phase substantially overlap.

15. The method of claim 12, wherein the ionization device is an ultraviolet (UV) lamp projecting UV light into the detecting region, and gas molecules with an ionization potential lower than the UV light are ionized.

16. The method of claim 12, wherein the switch is a single pole double throw switch having an input side with a single input connector and an output side having a first output connector and a second output connector, and wherein the single input connector is electrically connected to the second interdigital pole, the first output connector is electrically connected to the compensation voltage source, and the second output connector is electrically connected to the processing device.

17. The method of claim 12, wherein the separation voltage source provides an alternating current to the first interdigital pole during the separation phase and the separation voltage source otherwise supplies a constant direct current voltage to the first interdigital pole.

18. The method of claim 12, wherein the compensation voltage source is a direct current voltage.

19. The method of claim 12, wherein the detection phase further comprises altering the second direct current voltage that is supplied to the second interdigital pole.

20. A computer program product for detecting volatile organic compounds (VOCs) in a gas diffused into a detecting region of a VOC sensor, the computer program product comprising at least one non-transitory computer-readable storage medium having computer-readable program code portions stored therein, the computer-readable program code portions comprising an executable portion configured to:

execute an ionization phase comprising:

enabling an ionization device and creating a plurality of ionized gas molecules;

execute a separation phase comprising:

causing a separation voltage to be supplied to a first interdigital pole disposed within the detecting region and electrically connected to a separation voltage source; and causing a compensation voltage to be supplied to a second interdigital pole disposed within the detecting region and electrically connected to a compensation voltage source through a switch;

disable the ionization device upon completion of the ionization phase;

execute a detection phase comprising:

toggling the switch to electrically connect the second interdigital pole to a processing device; and causing a first direct current voltage to be supplied to the first interdigital pole and cause a second direct current voltage to be supplied to the second interdigital pole; and determine a VOC value representative of a number of volatile organic compounds in the gas based at least in part on a number of ionized gas molecules that contact the second interdigital pole while the second interdigital pole is electrically connected to the processing device.

\* \* \* \* \*